US009180148B2

(12) United States Patent
Naidu et al.

(10) Patent No.: US 9,180,148 B2
(45) Date of Patent: *Nov. 10, 2015

(54) METALLO-LACTOFERRIN-COENZYME COMPOSITIONS AND METHODS FOR WEIGHT MANAGEMENT

(71) Applicant: Naidu LP, Pomona, CA (US)

(72) Inventors: A. Satyanarayan Naidu, Anaheim Hills, CA (US); A. G. Tezus Naidu, Anaheim Hills, CA (US); A. G. Sreus Naidu, Anaheim Hills, CA (US)

(73) Assignee: NAIDU LP, Yorba Linda, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 13/932,494

(22) Filed: Jul. 1, 2013

(65) Prior Publication Data

US 2013/0295069 A1 Nov. 7, 2013

Related U.S. Application Data

(60) Division of application No. 13/096,398, filed on Apr. 28, 2011, now Pat. No. 8,476,223, which is a continuation-in-part of application No. 11/442,473, filed on May 26, 2006, now Pat. No. 7,956,031.

(60) Provisional application No. 60/686,257, filed on May 31, 2005.

(51) Int. Cl.

| A61K 38/40 | (2006.01) |
|---|---|
| A61K 38/43 | (2006.01) |
| A61K 35/745 | (2015.01) |
| A23L 1/03 | (2006.01) |
| A23L 1/29 | (2006.01) |
| A23L 1/30 | (2006.01) |
| A23L 1/302 | (2006.01) |
| A23L 1/304 | (2006.01) |
| A23L 1/305 | (2006.01) |
| A23L 1/308 | (2006.01) |
| A61K 9/00 | (2006.01) |
| A61K 9/16 | (2006.01) |
| A61K 31/715 | (2006.01) |
| A61K 31/718 | (2006.01) |
| A61K 31/737 | (2006.01) |
| A61K 36/185 | (2006.01) |
| A61K 36/27 | (2006.01) |
| A61K 36/48 | (2006.01) |
| A61K 36/54 | (2006.01) |
| A61K 36/55 | (2006.01) |
| A61K 36/68 | (2006.01) |
| A61K 38/44 | (2006.01) |

(Continued)

(52) U.S. Cl.
CPC ............... *A61K 35/745* (2013.01); *A23L 1/034* (2013.01); *A23L 1/293* (2013.01); *A23L 1/3002* (2013.01); *A23L 1/302* (2013.01); *A23L 1/304* (2013.01); *A23L 1/305* (2013.01); *A23L 1/3006* (2013.01); *A23L 1/308* (2013.01); *A23L 1/3014* (2013.01); *A23L 1/3051* (2013.01); *A23L 1/3056* (2013.01); *A61K 9/0095* (2013.01); *A61K 9/1617* (2013.01); *A61K 31/715* (2013.01); *A61K 31/718* (2013.01); *A61K 31/737* (2013.01); *A61K 35/747* (2013.01); *A61K 36/185* (2013.01); *A61K 36/27* (2013.01); *A61K 36/48* (2013.01); *A61K 36/54* (2013.01); *A61K 36/55* (2013.01); *A61K 36/68* (2013.01); *A61K 38/40* (2013.01); *A61K 38/44* (2013.01); *A61K 38/446* (2013.01); *A61K 38/47* (2013.01); *A61K 45/06* (2013.01); *A23V 2002/00* (2013.01)

(58) Field of Classification Search
CPC ........ A23L 1/304; A23L 1/293; A23L 1/3002; A23L 1/302; A23L 1/3056; A61K 38/40; A61K 45/06; A61K 31/715; A61K 9/0095; A23V 2002/00

See application file for complete search history.

(56) References Cited

U.S. PATENT DOCUMENTS

| 5,846,569 A | 12/1998 | Anderson et al. |
|---|---|---|
| 6,066,469 A | 5/2000 | Kruzel et al. |

(Continued)

FOREIGN PATENT DOCUMENTS

| JP | 02191205 | 7/1990 |
|---|---|---|
| JP | 10-236975 | 9/1998 |

(Continued)

OTHER PUBLICATIONS

Arnold, et al. "Engineered Metal-Binding Proteins: Purification to Protein Folding," Science, vol. 252, pp. 1796-1797, 1991.

(Continued)

*Primary Examiner* — Taeyoon Kim
(74) *Attorney, Agent, or Firm* — Knobbe, Martens, Olson & Bear, LLP

(57) ABSTRACT

Formulations are provided for the management of weight. The formulations generally include a trigger complex, an elemental complex and a coenzyme-vitamin B complex. The trigger complex is high in fiber such as glucomannan and includes Metallo-Lactoferrin protein in an alkaline buffer system. The elemental complex includes one or more trace element as a suitable salt. The coenzyme-vitamin B complex includes one or more coenzyme, coenzyme precursor and/or B-vitamin. The compositions may optionally include additional components such as dihydroxy acetone (DHA), inositol, 5-hydroxy-L-tryptophan (5-HTP), choline, milk protein hydrolysate, and pyruvate. The compositions can be administered orally in a variety of forms and may substitute for one or more meals per day to manage weight.

16 Claims, No Drawings

(51) Int. Cl.
*A61K 38/47* (2006.01)
*A61K 45/06* (2006.01)
*A61K 35/747* (2015.01)

(56) References Cited

U.S. PATENT DOCUMENTS

| | | | |
|---|---|---|---|
| 6,172,040 B1 | 1/2001 | Naidu | |
| 6,267,985 B1 | 7/2001 | Chen et al. | |
| 6,294,579 B1 | 9/2001 | Carnazzo | |
| 6,492,429 B1 | 12/2002 | Graus et al. | |
| 6,572,868 B1 | 6/2003 | Cope | |
| 6,645,472 B1 | 11/2003 | Anderson | |
| 7,125,963 B2 | 10/2006 | Naidu | |
| 7,445,807 B2 | 11/2008 | Lockwood | |
| 7,601,689 B2 | 10/2009 | Naidu | |
| 7,956,031 B2 | 6/2011 | Naidu et al. | |
| 8,003,603 B2 | 8/2011 | Naidu | |
| 8,021,659 B2 | 9/2011 | Naidu et al. | |
| 8,703,699 B2 | 4/2014 | Cornish et al. | |
| 2002/0044913 A1 | 4/2002 | Hamilton | |
| 2003/0170290 A1 | 9/2003 | Shug et al. | |
| 2004/0043922 A1 | 3/2004 | Naidu | |
| 2004/0052860 A1 | 3/2004 | Reid et al. | |
| 2004/0071825 A1* | 4/2004 | Lockwood | 426/72 |
| 2004/0214750 A1 | 10/2004 | Georgiades | |
| 2005/0106194 A1 | 5/2005 | Schiltz | |
| 2005/0175597 A1 | 8/2005 | Rawlin et al. | |
| 2005/0176123 A1 | 8/2005 | Katunuma | |
| 2005/0186319 A1 | 8/2005 | Williams et al. | |
| 2006/0240116 A1 | 10/2006 | Jolley | |
| 2008/0254018 A1 | 10/2008 | Naidu | |
| 2009/0148433 A1 | 6/2009 | Naidu et al. | |
| 2011/0286986 A1 | 11/2011 | Naidu et al. | |
| 2011/0286989 A1 | 11/2011 | Naidu | |

FOREIGN PATENT DOCUMENTS

| | | |
|---|---|---|
| WO | WO 01/15715 | 3/2001 |
| WO | WO 2004/093995 | 11/2004 |
| WO | WO 2005/063184 | 7/2005 |
| WO | WO 2005/079764 | 9/2005 |
| WO | WO 2006/009825 | 1/2006 |

OTHER PUBLICATIONS

Baker, et al. "Molecular Structure, Binding Properties and Dynamics of Lactoferrin," Cell. Mol. Life Sci., vol. 62, pp. 2531-2539, 2005.
Colostrum Prime Life™. Downloaded from http://www.jarrow.com/product/207/Colostrum_Prime_Life. pp. 1-2, 2008.
Dworak, et al., Sleep and Brain Energy Levels: ATP changes during sleep, *J. Neurosci*, 30(26) : 9007-9016, Jul. 30, 2010.
Specifications and Analysis of Bovine Colostrum. Downloaded from www.scheitificneutraceuticals.com/assay.htm pp. 1-3, 2008.
Baldwin et al., "The Effect of Human Serum Transferrin and Milk Lactoferrin on Hydroxyl Radical Formation from Superoxide and Hydrogen Peroxide," *The Journal of Biological Chemistry*, vol. 259*21), pp. 13391-13394 (1984).
Bannister et al., "Enhanced Production of Hydroxyl Radicals by the Xanthine-Xanthine Oxidase Reaction in the Presence of Lactoferrin," *Biochimica et Biophysica Acta*, vol. 715, pp. 116-120 (1982).
Czirok et al., "In vitro and in vivo (LD50) effects of human lactoferrin on bacteria," *Acta Microbiol Hung*., vol. 37(1), pp. 55-71 (1990) (Abstract).
Dionysius et al., "Forms of Lactoferrin: Their Antibacterial Effect on Enterotoxigenic *Escherichia coli*," *Journal of Dairy Science*, vol. 76(9), pp. 2597-2606 (1993).
Harris, "Binding and Transport of Nonferrous Metals by Serum Transferrin," *Structure and Bonding*, vol. 92, pp. 122-162 (1998).
Harris, "Thermodynamic binding constants of the zinc-human serum transferrin complex," *Biochemistry*, vol. 22(16), pp. 3920-3926 (1983).
Jabeen et al., "Structure of the zinc-saturated C-terminal lobe of bovine lactoferrin at 2.0Å resolution," *Acta Cryst.*, vol. D61, pp. 1107-1115 (2005).
Klebanoff et al., "Prooxidant Activity of Transferrin and Lactoferrin," *J. Exp. Med.*, vol. 172, pp. 1293-1303 (Nov. 1990).
Li et al., "Rationalization of the strength of metal binding to human serum transferrin," *Eur. J. Biochem.*, vol. 242, pp. 387-393 (1996).
Newsome et al., "Apolactoferrin inhibits the catalytic domain of matrix metalloproteinase-2 by zinc chelation," *Biochem. Cell Biol.*, vol. 85, pp. 563-572 (2007).
Powell, "The Antioxidant Properties of Zinc[1,2]," *The Journal of Nutrition*, Supplement, pp. 1447S-1454S (Jun. 3, 2009).
Sun et al., "Rationalisation of Metal Binding to Transferrin: Prediction of Metal-Protein Stability Constants," *Structure and Bonding*, vol. 88, pp. 72-102 (1997).
Winterbourn, "Lactoferrin-catalysed hydroxyl radical production," *Biochem. J.*, vol. 210, pp. 15-19 (1983).
Azari et al., "A simple and Rapid Procedure for Preparation of Large Quantities of Pure Ovotransferrin," *Arch Biochem Biophys*, vol. 118, pp. 138-144 (1967).
Bodin et al., "ATP-Stimulated Release of ATP by Human Endothelial Cells," *J Cardiovascular Pharmacol*, vol. 27(6), pp. 872-875 (Jun. 1996).
Mazurier et al., "Comparative study of the iron-binding properties of human transferrins. I. Complete and sequential iron saturation and desaturation of the lactotransferrin," *Biochem Biophys Acta*, vol. 629, pp. 399-408 (1980).

* cited by examiner

METALLO-LACTOFERRIN-COENZYME COMPOSITIONS AND METHODS FOR WEIGHT MANAGEMENT

CROSS-REFERENCE TO RELATED APPLICATIONS

This application is a divisional of U.S. application Ser. No. 13/096,398, filed Apr. 28, 2011 which is a continuation-in-part of U.S. application Ser. No. 11/442,473, filed May 26, 2006 which claims priority of U.S. Provisional Application No. 60/686,257, filed May 31, 2005, which is incorporated herein by reference.

BACKGROUND OF THE INVENTION

1. Field of the Invention

This invention describes methods to prepare specific combinations of metallo-lactoferrin (LF)-coenzyme mixtures to trigger the release of bioenergy (bio-E) in the form of adenosine triphosphate (ATP). Additionally the invention discloses compositions of functional delivery systems to recreate physiological proton gradients for rapid activation and release of cellular and extracellular ATP.

2. Description of the Related Art

All living organisms, plants and animals, operate a power house of bio-E for physiological functions. The bio-E is required for metabolic processes that keep organisms alive. Some of these processes occur in a continuous manner, such as the metabolism of nutrients, synthesis of essential biological molecules (i.e. proteins and DNA), active transport of molecules and ions in/out of the organism. Other processes occur only at specific times, such as a muscle contraction or other cellular movements. Animals obtain their energy by chemo-oxidation of nutrients in the mitochondria, where as plants do so by photo-oxidation, trapping the sunlight using chlorophyll. However, this trapped energy is useful only when it is further transformed into a bio-compatible form that the organism could easily utilize. This specific energy transformer is essentially a nucleotide, the adenosine triphosphate or ATP.

ATP, the bio-E currency or unit, transfers energy from chemical bonds to endergonic (energy absorbing) reactions within the cell. Structurally, ATP consists of the adenine nucleotide (ribose sugar, adenine base, and phosphate group, $PO_4^{-2}$) plus two other phosphate groups. Energy is stored in the covalent bonds between phosphates, with the highest amount of energy (~7 kcal/mole) in the bond between the second and third phosphate groups. This covalent bond is known as the pyrophosphate bond. Following is the chemical equation for ATP formation: ADP+Pi+ΔE→ATP. The chemical equation for expenditure/release of ATP energy is: ATP→ADP+ΔE+Pi. Thus, the function of ATP to release energy is dependent on losing the endmost phosphate group (covalent bond) by hydrolysis. This enzymatic reaction with ATP releases the bio-compatible energy for cellular processes. The metabolic end product of this process is adenosine diphosphate or ADP, and the phosphate group either ends up as an orthophosphate ($HPO_4$) or attached to another molecule (such as an alcohol). Even more bio-E can be extracted from ATP by dissociating the second phosphate group to produce adenosine monophosphate or AMP. Energy is not immediately needed when an organism is resting. Accordingly, the reverse reaction takes place and the phosphate group is reattached to the ADP using energy obtained from chemo- or photo-oxidation. Therefore, the ATP molecule acts as a chemical transformer, storing energy when it is not needed, but capable to release the bio-E instantly when required by the organism.

The enzyme that makes ATP is the ATPase or ATP synthase, which is present in the mitochondria of animal cells or chloroplasts in plant cells. The energy requiring step in making ATP is not the synthesis from ADP and phosphate, but the initial binding of the ADP and the phosphate to the enzyme. The ATPase enzyme promotes ion transport through membranes and the phosphate group that is ripped from ATP binds directly to the enzyme. Two processes convert ADP into ATP: 1) substrate-level phosphorylation that occurs in the cytoplasm when ATPase attaches a third phosphate to the ADP; and 2) chemiosmosis, which is comprised of several enzymes arranged in an electron transport chain (ETC) embedded in a membrane. In eukaryotes this membrane is either in the chloroplast or mitochondrion. During chemiosmosis, $H^+$ ions (protons) are pumped across the membrane into a confined space that contains numerous hydrogen ions. The energy for pumping comes from the coupled oxidation-reduction reactions in the ETC. Electrons are passed from one membrane-bound enzyme to another, losing some energy with each transfer (as per the second law of thermodynamics). This lost energy allows the pumping of protons against the concentration gradient (there are fewer protons outside than inside of the confined space). The confined protons are restricted to pass back through the membrane. Therefore, their only exit is through the enzyme ATPase, which is located in the confining membrane. As the proton passes through the ATPase, energy from the enzyme is transferred to attach a third phosphate to ADP, converting it to ATP.

Generation of bio-E is dependent on three important factors: 1) the elemental complex (i.e. metal ions $Fe^{3+}$, $Cu^{2+}$, $Cr^{2+}$, $Zn^{2+}$ and $Mg^{2+}$) for biosynthesis and function of coenzymes; 2) the coenzyme complex (i.e. coenzyme Q10, nicotinamide adenosine dinucleotide or NADH, Flavones, B-complex vitamins) for transport of charged electrons during oxidative phosphorylation; and 3) the trigger complex (i.e. ATPase and a proton gradient equipped with scavenging and protection against free radicals).

Among the elemental complex, iron is the critical component for the bio-E pathways including the coupling of inorganic phosphate to ADP to form ATP in living organisms. Iron is the most abundant transition metal in mammals and humans and exists in two oxidative states in aqueous solutions, ferrous ($Fe^{2+}$) and ferric ($Fe^{3+}$), which allows this metal ion to participate in a broad range of chemical reactions from +350 mV to −500 mV. Such intracellular reactions include the oxidative catalysis of oxygen and hydrogen peroxide, the decomposition of peroxide and superoxide, and oxidative phosphorylation. In the respiratory, photosynthetic and microsomal ETC, iron exists in cytochromes (of the types a, b, c and d) as well as iron-sulfur proteins. Other iron-sulfur proteins catalyze oxidation reactions (xanthine oxidase, xanthine dehydrogenase, aldehyde oxidase and sulfite oxidase) and the Krebs cycle enzyme aconitase. Iron is a critical co-factor for the enzyme RNA reductase during DNA synthesis. Iron reduces the nucleotides ADP, uridine diphosphate (UDP), cytosine diphosphate (CDP) and guanine diphosphate (GDP), forming precursors for the DNA (Jacobs A, Worwood M (ed). Iron in biochemistry and Medicine. Academic Press, NY, pp 529-572, 1980; Crichton R R, Charloteaux-Wauters M. Iron transport and storage. Eur J Biochem 164:485-506, 1987).

Copper is the second important component of the elemental complex, which acts as a catalytic agent via many copper metalloenzymes which act as oxidases. Amine oxidases are important in a variety of physiological processes. Ferroxidases, copper enzymes in the plasma, are required for ferrous iron oxidation and binding of iron to transferrin. The main copper protein in plasma, ferroxidase I (or ceruloplasmin), is a potent antioxidant. Another copper enzyme, cytochrome c oxidase, is a mitochondrial enzyme that catalyzes the reduction of oxygen to water to fuel ATP synthesis. Cytochrome c oxidase is most abundant in highly metabolic tissues, including the heart, brain, and liver. Other copper enzymes are responsible for precursors of dopa and melatonin formation, conversion of dopamine to norepinephrine, production of amides, and protection from free radical damage.

Another component of the elemental complex, zinc ($Zn^{2+}$) is a catalyst for more than 300 enzymes as well as a cofactor for DNA, RNA, and protein synthesis. Manganese ($Mn^{2+}$) is required for several metabolic pathways involved in amino acid, cholesterol, and carbohydrate metabolism. Manganese metalloenzymes include arginase, phosphoenolpyruvate decarboxylase, glutamine synthetase, and manganese superoxide. Chromium ($Cr^{2+}$) as referred to as glucose tolerance factor (GTF) potentiates glucose uptake by cells, oxidation of glucose, and incorporation of glucose into fatty acids and cholesterol. Finally, magnesium ($Mg^{2+}$) is required in the formation of cyclic AMP (cAMP) and for ionic movements across cell membranes. It is also involved in protein synthesis and carbohydrate metabolism. (Shils M, Olson A, Shike M. Modern nutrition in health and disease. $8^{th}$ ed. Philadelphia, Pa.: Lea and Febiger, 1994; Covington T R, et al., Handbook of nonprescription drugs, Washington D.C.: Am Pharmaceutical Assn, 1996; 945, 272; Vincent J B. The biochemistry of chromium. J Nutr 130:715-718, 2000).

Among the coenzyme/vitamin-B complex, coenzyme Q is an essential part of the cellular machinery to produce ATP and provides bio-E for vital cellular functions. The major part of ATP production occurs in the inner membrane of mitochondria, where coenzyme Q is found. Coenzyme Q has a unique function since it transfers electrons from the primary substrates to the oxidase system at the same time that it transfers protons to the outside of the mitochondrial membrane. This transfer results in a proton gradient across the membrane. As the protons return to the interior through the enzymatic machinery for making ATP, they drive the formation of ATP. Coenzyme Q is bound to the oriented enzymatic protein complexes. It is oxidized and releases protons to the outside and picks up electrons and protons on the inside of the mitochondrial membrane. There are two protein complexes in the membrane where electrons and protons are transferred through coenzyme Q. The first is the primary reductase where coenzyme Q is reduced by NADH (complex I). During the reduction process four protons are transported across the membrane for every coenzyme Q reduced. It has been suggested that coenzyme Q is reduced and reoxidized in the complex twice before electrons are transferred to a second loosely bound coenzyme Q to form quinol which can travel through the lipid in the membrane to a second complex where the quinol is oxidized again (complex III) with transfer of protons across the membrane. The details of quinol binding and oxidation at the binding site in this complex are well known. As in complex I, there is a cyclic oxidation-reduction-reoxidation with the oxidation and proton release step always on the outside so that protons are released in the right direction. Again the oxidation-reduction cycle allows for four protons to cross the membrane for each quinol oxidation cycle. The quinone cycle thus doubles the efficiency of the coenzyme Q in building up the proton charge across the membrane which allows twice as much ATP production than a simple one step oxidation of quinol. After the cycle is completed the oxidized quinone migrates through the membrane to be re-reduced at complex I. A simpler form of energy conversion based on coenzyme Q reduction-oxidation is found in lysosomes. In this case the quinol transfers a proton across the lysosomal membrane to acidify the inside which involves energy input to work against a proton gradient. No ATP can be formed since the lysosomal membrane does not have a proton driven ATP synthetase. The acidification of the lysosome activates hydrolytic enzymes for digestion of cellular debris. In other words, coenzyme Q energizes cell house cleaning. Details of the enzymes and possible coenzyme Q binding sites in the lysosomal membrane are not known. The enzyme complex in the membrane involves reduction of coenzyme Q by NADH in the cytoplasm and reoxidation of the quinol by oxygen (Brandt U: Proton translocation in the respiratory chain involving ubiquinone—a hypothetical semiquinone switch mechanism for complex I. Biofactors 9: 95-102, 1999; Yu C A, Zhang K-P, Deng H, Xia D, Klm H, Deisenhofer J, Yu L: Structure and reaction mechanisms of the multifunctional mitochondrial cytochrome bc1 complex. Biofactors 9: 103-110, 1999; Gille L, Nohl H. The existence of a lysosomal redox chain and the role of ubiquinone. Arch Biochem Biophys 375: 347-354, 2000).

Coenzyme 1, or NADH, is the active coenzyme form of vitamin B3. NADH is a natural substance found in most life forms and is necessary for energy production. NADH provides input to the respiratory chain from the NAD-linked dehydrogenases of the citric acid cycle. The complex couples the oxidation of NADH and the reduction of coenzyme Q, to the generation of a proton gradient which is then used for ATP synthesis. NADH is located both in the mitochondria and cytosol of cells. It is a dinucleotide comprised of the nucleotide adenylic acid and a second nucleotide in which nicotinamide, a B vitamin, is the nitrogenous base. NADH is a key member of the ETC in mitochondria. The nicotinamide moiety is the portion of the dinucleotide that undergoes reversible reduction. NADH is the reduced form of the dinucleotide. The passage of electrons along the ETC is coupled to the formation of ATP by the oxidative phosphorylation process. The mitochondrial membrane is impermeable to NADH, and this permeability barrier effectively separates cytoplasmic NADH from the mitochondrial NADH pools. However, cytoplasmic NADH can be used for bio-E production. This occurs when the malate-aspartate shuttle introduces reducing equivalents from NADH in the cytosol to the ETC of the mitochondria.

Biotin (coenzyme R) is mitochondrial reserve that acts as a coenzyme in bicarbonate-dependent carboxylation reactions. Biotin-containing enzymes are involved in gluconeogenesis, fatty acid synthesis, propionate metabolism, and the catabolism of leucine. Pyruvate decarboxylase is a biotin-dependent enzyme (Bonjour J P. Biotin in human nutrition. Ann NY Acad Sci 447:97-104, 1985).

Among the B-complex vitamins, thiamine (vitamin B1) is required for carbohydrate metabolism. It combines with ATP to form thiamine diphosphate, a coenzyme in carbohydrate metabolism that facilitates the decarboxylation of pyruvic acid and α-ketoglutaric acid. This coenzyme is also a part of transketolation reactions. Thiamine is also a coenzyme in the utilization of pentose in the hexose monophosphate shunt.

Riboflavin (vitamin B2) is required for tissue respiration. It is converted to the coenzyme riboflavin 5-phosphate (flavin mononucleotide, FMN) and then to the coenzyme flavin adenine dinucleotide (FAD). These act as hydrogen carriers for several enzymes known as flavoproteins, which are involved in oxidation-reduction reactions of organic substrates and in intermediary metabolism. Riboflavin is a cofactor for various respiratory enzymes such as glutaryl coenzyme A dehydrogenase, erythrocyte glutathione reductase, sarcosine dehydrogenase, electron transferring flavoprotein (ETF) dehydrogenase, and NADH dehydrogenase.

Niacin-Niacinamide (vitamin B3) includes niacin (nicotinic acid) and niacinamide (nicotinamide). The term niacin refers specifically to nicotinic acid, but is also used collectively to refer to both nicotinic acid and nicotinamide. Niacinamide is required for lipid metabolism, tissue respiration, and glycogenolysis. Niacinamide is incorporated into the coenzymes, NAD and NADP that act as hydrogen-carrier molecules.

Pantothenic acid (vitamin B5) is required for intermediary metabolism of carbohydrates, proteins and lipids. It is a precursor of coenzyme A, which is required for acetylation reactions in gluconeogenesis, in the release of bio-E from carbohydrates, the synthesis and degradation of fatty acids, and the synthesis of sterols, steroid hormones, porphyrins, acetylcholine and other compounds. Pantothenic acid also appears to be essential to normal epithelial function.

Pyridoxine (vitamin B6) is required for amino acid metabolism. It is also involved in carbohydrate and lipid metabolism. In the body, pyridoxine is converted to coenzymes pyridoxal phosphate and pyridoxamine phosphate, in a wide variety of metabolic reactions. These reactions include transamination of amino acids, conversion of tryptophan to niacin, synthesis of gamma-aminobutyric acid (GABA) in the central nervous system, metabolism of serotonin, norepinephrine and dopamine, metabolism of polyunsaturated fatty acids and phospholipids, and the synthesis of heme, a hemoglobin constituent. Pyridoxine is involved with several of the reactions important for the overall metabolism of nitrogen; therefore, pyridoxine requirements are related to the total amino acid nitrogen burden to be metabolized. Pyridoxine is also a cofactor for enzymes involved in one of two pathways for the metabolism of homocysteine.

Folic acid (vitamin B9) converts to tetrahydrofolate after physiological absorption. In humans, tetrahydrofolate-based coenzymes play a major role in intracellular metabolism and in the rate-limiting steps of DNA synthesis. Folic acid is also involved in the metabolism of homocysteine.

Cobalamin (vitamin B12) is required for nucleoprotein and myelin synthesis, cell growth reproduction, and erythropoiesis. Synthetic vitamin B12 (cyanocobalamin and methylcobalamin) converts to coenzyme B12, which is essential for the conversion of methylmalonate to succinate, and the synthesis of methionine from homocysteine. Vitamin B12 is involved in maintaining sulfhydryl groups in the reduced form required by enzymes involved in fat and carbohydrate metabolism and protein synthesis.

SUMMARY OF THE INVENTION

Further aspects, features and advantages of this invention will become apparent from the detailed description of the preferred embodiments which follow.

Embodiments of the invention are directed to compositions having the following components:
 a trigger complex which includes a metal-binding protein and at least one hydrocolloid compound at alkaline pH,
 an elemental complex which includes at least one metal salt, and
 a coenzyme complex which includes at least one coenzyme or coenzyme precursor.

In preferred embodiments, the metal-binding protein may be selected from transferrin, ovotransferrin, ceruloplasmin and lactoferrin. In a more preferred embodiment, the metal-binding protein is lactoferrin. In yet more preferred embodiments, the metal-binding protein is Fe(III)-lactoferrin, Cu(II)-lactoferrin or Zn(II)-lactoferrin. In a most preferred embodiment, the lactoferrin is lactoferrin-(TCR).

Preferably, the hydrocolloid compound(s) of the trigger complex are selected from edible celluloses, arabinogalactans, β-glucans, arabinoxylans, glucuronoxylans, xyloglucans, galactomannans, methyl cellulose, hydroxypropylmethyl cellulose (HPMC), inulin, oligofructans, xanthan gum, guar gum, locust bean gum, gum acacia, gum karaya, gum tragacanth, resistant starches, maltodextrins, chemically synthesized polydextrose, lactulose, cellulose derivatives, methyl cellulose, hydroxypropylmethylcellulose, egg lecithin, soybean lecithin, vegilecithin, vitellin, short chain fructooligosaccharides (FOS), transgalactooligosaccharides (TOS), levan, oligofructose, xylooligosaccharides (XOS), curdlan, chitin, chitosan, collagen and chondroitin. More preferably, the hydrocolloid includes maltodextrins, chitin, chitosan, cellulose derivatives, glucomannan, guar gum, locust bean gum, prickly pear cactus and combinations thereof.

In preferred embodiments, an alkaline pH is provided by a carbonate/bicarbonate buffer system.

Preferably, the elemental complex includes one or more metal salts such as iron, copper, zinc, manganese, and chromium.

In preferred embodiments, the coenzyme complex includes one or more cofactor(s) such as coenzyme Q10, NADH, NADPH, coenzyme R and B-complex vitamins. In preferred embodiments, the B-complex vitamins are Vitamin B1, Vitamin B2, Vitamin B3, Vitamin B5, Vitamin B6, Vitamin B9, Vitamin B12, or combinations thereof.

In some preferred embodiments, compositions according to the invention additionally include D-ribose, L-arginine, L-carnitine or combinations thereof.

Preferred embodiments of the invention include a food or beverage which includes any of the compositions described above.

Preferred embodiments of the invention are directed to compositions which include:
 an elemental complex having at least one component selected from iron, copper, zinc, chromium and manganese;
 a coenzyme complex which includes one or more of coenzyme Q10, coenzyme R, Vitamin B1, Vitamin B2, Vitamin B3, Vitamin B5, Vitamin B6, Vitamin B9, and Vitamin B12; and
 a trigger complex which includes a dietary fiber, lactoferrin and a bicarbonate buffer.

In preferred embodiments, additional components are selected from D-ribose, L-arginine, and L-carnitine or derivatives thereof.

In preferred embodiments, the dietary fiber includes maltodextrin, glucomannan, guar gum, locust bean gum, prickly pear cactus and combinations thereof.

In preferred embodiments, the lactoferrin is lactoferrin-(TCR).

Preferred embodiments of the invention are directed to formulations for weight management which include the elemental complex, the coenzyme complex and the trigger complex as described above, and additional components selected from: dihydroxy acetone, inositol, 5-HTP, choline, milk protein concentrate, and pyruvate.

Preferred embodiments of the invention are directed to formulations for exercise recovery which include the elemental complex, the coenzyme complex and the trigger complex as described above, and additional components selected from the following ingredients: L-taurine, N-acetyl creatine, dehydroepiandrosterone (DHEA), one or more amino acids, choline, inositol hexanicotinate, and protein powder.

Preferred embodiments of the invention are directed to formulations for diabetes control which include the elemental complex, the coenzyme complex and the trigger complex as described above, and additional components selected from the following ingredients: chromium, magnesium, banaba leaf extract, cinnamon bark extract, fenugreek extract, and gymnema leaf extract. More preferably, the lactoferrin concentration of the trigger complex is 50-500 mg per serving.

Preferred embodiments of the invention are directed to formulations for control of hyperlipidemia which include the elemental complex, the coenzyme complex and the trigger complex as described above, and additional components selected from the following ingredients: policosanol, sitostanol, octacosanol, flaxseed oil and blond psyllium.

Preferred embodiments of the invention are directed to formulations for immuno-compromised conditions which include the elemental complex, the coenzyme complex and the trigger complex as described above, and additional components selected from the following ingredients: superoxide dismutase, lysozyme, lactoperoxidase, l-theanine, vitamin-E, and blond psyllium.

Preferred embodiments of the invention are directed to formulations for detoxification support which include the elemental complex, the coenzyme complex and the trigger complex as described above, and additional components selected from the following ingredients: *Lactobacillus* spp., *Bifidobacterium* spp., L-theanine, cranberry root extract, turmeric root extract, inulin and blond psyllium.

Embodiments of the invention are directed to a method of weight management which includes administering a weight loss bar which includes the elemental complex, the coenzyme complex and the trigger complex as described above, and additional components selected from: dihydroxy acetone, inositol, 5-HTP, choline, milk protein concentrate, and pyruvate, as a meal supplement.

Embodiments of the invention are directed to a method of weight management which includes the steps of mixing the weight loss formulation described above which includes the elemental complex, the coenzyme complex and the trigger complex as described above, and additional components selected from: dihydroxy acetone, inositol, 5-HTP, choline, milk protein concentrate, and pyruvate, with milk or water and drinking the mixture as a meal supplement.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

DEFINITIONS

The term "coenzyme" has its usual and customary meaning and refers to a small molecule (not a protein but sometimes a vitamin) essential for the activity of some enzymes.

The term "NADH" has its usual and customary meaning as the reduced form of nicotinamide adenine dinucleotide and also refers to the active coenzyme form of Vitamin B3.

The term "Flavone" refers to a class of plant secondary metabolites based around a phenylbenzopyrone structure having antioxidant activity.

The term "B-vitamin" has its usual and customary meaning and includes any B-vitamin including but not limited to vitamin B1 (thiamine), vitamin B2 (riboflavin), vitamin B3 (niacin/niacinamide), vitamin B5 (pantothenic acid), vitamin B6 (pyridoxine), vitamin B9 (folic acid), and vitamin B12 (cobalamin).

The term "Metalloenzyme" has its usual and customary meaning and refers generally to an enzyme containing a bound metal atom (e.g., cobalt, copper, iron, molybdenum, or zinc) as an integral part of its structure. Specific examples include iron metalloenzymes such as lactoferrin and transferrin; copper containing metalloenzymes such as ferroxidase I, ceruloplasmin, and cytochrome c oxidase; and manganese metalloenzymes such as arginase, phosphoenolpyruvate decarboxylase, glutamine synthetase and manganese superoxide.

The term "coenzyme Q", also known as "ubiquinone" or "ubiquinol", has its usual and customary meaning and refers to a biologically active quinone with an isoprenoid side chain. The various kinds of Coenzyme Q can be distinguished by the number of isoprenoid side chains they have. The most common CoQ in human mitochondria is Q10.

The term "biotin" (coenzyme R) has its usual and customary meaning and refers to a coenzyme in bicarbonate-dependent carboxylation reactions.

The term "trigger complex" as used herein refers to a composition that contains at least one metal-transport protein such as lactoferrin, transferrin, ovotransferrin, or ceruloplasmin; and one or more hydrocolloid compounds in an alkaline buffer system.

The term "elemental complex" as used herein refers to a complex of trace elements in appropriate salt forms. These elements may include but are not limited to iron, copper, zinc, manganese, and/or chromium.

The term "coenzyme/vitamin B complex" as used herein refers to a complex of coenzymes/coenzyme precursor and B vitamins which may include but are not limited to one or more of coenzyme Q10, coenzyme R and B-complex vitamins.

The term "hydrocolloid" is a substance that forms a gel with water and as used herein has its usual and customary meaning which specifically includes dietary fiber compounds.

Embodiments of the invention are directed to methods to formulate compositions for release of bio-E in the form of ATP.

One object of the present invention is to provide an energy composition, which gives a direct increase of the intracellular level of ATP. The bio-E formulations are suitable for several applications, including but not limited to human and animal health, weight loss, support for diabetic and pre-diabetic conditions, control of hyperlipidemia, support for patients suffering from low energy as a disease side effect (eg. AIDS), chronic fatigue syndrome, neutropenia, post-radiation treatment effects, celiac disease, and support for patients undergoing withdrawal and/or detoxification.

In preferred embodiments, bio-E formulations may include one or more of the following complexes: a trigger complex, and an elemental complex, and a coenzyme/vitamin-B complex.

In preferred embodiments, the trigger complex includes a metal-transport protein such as lactoferrin, transferrin, ovotransferrin, and ceruloplasmin. However, any protein that functions to transport essential metals such as iron(III), copper(II), Zn(II), Mn(II) and Cr(II), may be used as a protein component of the trigger complex. In a most preferred embodiment, the trigger complex includes lactoferrin.

Lactoferrin (LF) is an iron-binding glyco-protein present in milk and various mammalian secretions (e.g. saliva, tears, mucus, and seminal fluids). Crystallographic studies of LF indicate a bilobate structure (N-terminus and C-terminus lobes) with one iron-binding site in each lobe. LF has ability to reversibly bind two $Fe^{3+}$ ions per lobe in coordination with two $CO_3^{2-}$ ions.

LF has been found to be an excellent component for the trigger complex. The N- and C-lobes of LF bind/release iron, as well as copper or other essential metal ions over a broad range of pH (acid-alkaline) conditions. As discussed above, metal ions are an essential component of physiological energy production. Iron is a component of cytochromes, and Rieske proteins involved in electron transport as well as Fe—S proteins. While iron and other essential metal ions can be added with dietary supplements, this added iron is not necessarily bioavailable. LF has the physiological role to scavenge and release metal ions, particularly iron, as needed in the body. Therefore, supplying metal ions bound to LF assures that these metal ions will be bioavailable.

In addition, as LF binds metal ions in a reversible manner, iron bound to LF complex will not be dissociated where release would be unfavorable. It is particularly important that the concentration of the metal ions is in an optimal range. If the concentration is too high, the metal ion may act as an enzyme inhibitor. If the concentration is too low, then the metal ion becomes rate limiting. The inclusion of LF in the trigger complex assures that the metal ions will be provided within an optimal range.

Furthermore, LF demonstrates a potent antioxidant activity for extended periods of time, i.e. >48 h. This antioxidant activity of LF is important because free radicals such as superoxide and other reactive oxygen species are formed as a side product of the production of bio-E. LF provides an effective physiological free radical scavenging system. Furthermore, as the antioxidant function of LF relies upon reduction of iron to the ferrous form, LF, unlike plant-derived free radical scavengers, is recyclable and not readily depleted. Because of these properties, LF, when incorporated into the trigger complex, will effectively scavenge free radicals that are continuously generated by the electron transport chain (ETC), without any interference with ATP production.

LF also acts as an antimicrobial agent. In preferred embodiments, the ATP generation that is promoted by the bio-E formulations according to embodiments of the invention occurs in the stomach. Competition by the natural flora in the gut for ATP produced by the bio-E system is controlled by the antimicrobial function of LF present in the complex.

The LF useful in accordance with the present invention include LF isolated from mammalian sources (humans, cows, sows, mares, transgenic animals and the like), biological secretions such as colostrum, transitional milk, matured milk, milk in later lactation, and the like, or processed products thereof such as skim milk and whey. Also useful is recombinant LF produced in either prokaryotic and eukaryotic cells. The LF is isolated by any conventional method, such as by chromatography, ion-exchanger, molecular-sieve or affinity column. Suitable lactoferrin is available from various commercial sources (N-terminus or Glanbia from USA, Tatua or Fonterra from New Zealand, MG Nutritionals from Australia, Morinaga Milk Company from Japan, DMV International from the Netherlands). In preferred embodiments, the LF in the formulations described herein is non-immobilized, i.e. free dispersed native (fdn) form.

In most preferred embodiments, LF-"Treated for Contamination Reduction (TCR)", hereafter referred to as LF-TCR (as described in Naidu U.S. Pat. Appl. No. 20050197495, published Sep. 8, 2005) is suitable for the bio-E applications. Briefly, this TCR process includes the successive steps of treating a commercial LF preparation with a surfactant, an antioxidant and a polyphenol to form purified LF (LF-TCR). The LF preparation is mixed with the treatment agents. Typical surfactants include food-grade detergents, bile salts and plant saponins. Typical antioxidants which may be used include Vitamin A, Vitamin C, Vitamin E and metal chelators. Typical polyphenols include oleoresins, aquaresins, terpenes, flavonoids and biliproteins. The treated LF preparation is then dried to provide LF-TCR.

Preferably, the trigger complex also includes a strong alkaline system. In some embodiments, the buffer system is a carbonate/bicarbonate system, a Tris buffer system, a phosphate buffer system, a borate buffer system or a citrate buffer system. The buffers may be present as salts, preferably, salts of sodium, potassium or calcium Preferably, the buffer system provides a pH from 7.1-14.0, more preferably from 7.1-8.5.

In preferred embodiments, the trigger complex includes a hydrocolloid-base. Hydrocolloids are hydrophilic polymers, of vegetable, animal, microbial or synthetic origin, that generally contain many hydroxyl groups and may be polyelectrolytes. They are naturally present or added to control the functional properties of chemicals in an aqueous system. Most important amongst these properties are viscosity (including thickening and gelling) and water binding but also significant are many others including emulsion stabilization, prevention of ice recrystallization and organoleptic properties. Other more specialist applications include adhesion, suspension, flocculation, foam stabilization and film formation. Bioactive molecules are very complex chemicals and this together with the multifactorial functionality of the bio-E formulations several different hydrocolloids are required. Without intending to be bound by theory, it is postulated that the dietary fiber creates an interim pH gradient in a sponge or gel matrix due to the alkalinity of the trigger complex provided by the buffering agent. In the acidic environment of the stomach, a pH gradient is established. Conditions are then ideal for the generation of ATP. The acid-base interaction triggers the ETC, to initiate the ATP synthesis. In preferred embodiments the ATP synthase is provided by the endogenous ATP synthase present in the stomach, released from the interstitial lumen. In some preferred embodiments, an extract from yeast, preferably nutritional yeast or brewers' yeast, nutritional supplements which include chlorella or spirulina or the like is added to the bio-E formulation to further boost ATP synthase levels. While the gastric juice is acidic and the administration of any alkaline compound(s) into such milieu results in an instant neutralization reaction, certain dietary fibers slow down such acid-base titrations and establish an interim pH gradient.

Hydrocolloid compounds suitable for the establishment of pH gradients include but are not limited to, edible celluloses; hemicelluloses such as arabinogalactans, β-glucans, arabinoxylans, glucuronoxylans, xyloglucans, and galactomannans; cellulose derivatives such as methyl cellulose and hydroxypropylmethyl cellulose (HPMC); polyfructoses such as inulin and oligofructans; gums and mucilages such as xanthan gum, guar gum, locust bean gum, gum acacia, gum karaya, gum tragacanth; resistant starches and maltodextrins (both garden variety, Benefiber® and Fibersol® brand); chemically synthesized polydextrose; lactulose; cellulose derivatives (eg. methyl cellulose, hydroxypropylmethylcellulose); lecithins such as egg lecithin (ovolecithin), soybean lecithin, vegilecithin, and vitellin; short chain fructooligosaccharides (FOS); transgalactooligosaccharides (TOS); levan; oligofructose; xylooligosaccharides (XOS); curdlan; and fibers from animal origin such as chitin, chitosan, collagen and chondroitin.

In preferred embodiments, the bio-E formulations include an elemental complex. Preferably, the elemental complex includes trace metals in appropriate salt forms, which may include iron, copper, zinc, manganese, and/or chromium in preferred embodiments. In a most preferred embodiment, the metals are provided as covalently bound to LF. Iron, Copper, Zinc and other metal ions can be covalently bound to LF. As discussed above, when complexed with LF, the metal is in a bio-available form that can be used by the body. The elements are highly effective in the formulation when used as metallo-LF complexes, particularly, the Fe(III)-LF and Cu(II)-LF forms.

In preferred embodiments, the bio-E formulations include a coenzyme/vitamin-B complex. In preferred embodiments, the coenzyme/vitamin B complex includes one or more of coenzyme Q10, NADH, coenzyme R, and B-complex vitamins (B1, B2, B3, B5, B6, B9, B12). Furthermore, bioactive compounds such as D-ribose, L-arginine, and L-carnitine showed a potential overall synergy to enhance the ATP release when incorporated into the formulation. Inclusion of LF in the coenzyme/vitamin-B complex may facilitate bioavailability of these vitamin cofactors.

The trigger complex, LF in particular, in combination with specific coenzymes, including but not limited to coenzyme Q10, and NADH demonstrated a catalytic synergy in releasing cellular and extra-cellular ATP.

The bio-E formulations are suitable for delivery in various forms, including but not limited to tablets (chewables, effervescent), caplets, capsules, suppositories, powders, energy drinks, energy bars, patches, crème, infusions, and other forms that are commonly practiced in the art of manufacturing nutritionals, supplements and therapeutics for total body health and clinical nutrition. In some preferred embodiments, the bio-E formulation may be provided in either powdered or concentrated liquid form which is reconstituted by admixing the powdered or concentrated liquid composition with water. In some preferred embodiments, the bio-E formulation is flavored.

The bio-E formulations could be administered by various routes, the most preferred is oral, but also by other routes, including but not limited to sublingual, intravenous, intraperitoneal, intramuscular, subcutaneous and vaginal, for clinical nutrition (i.e. chronic fatigue syndrome, diabetes, HIV, cancer, post-operative recovery); sports nutrition (i.e. athletic performance, body building); and weight management.

The bio-E formulations may be formed by methods well known in the art. When preparing dosages forms incorporating the compositions of the present invention, the nutritional components are normally blended with conventional excipients such as binders, including gelatin, pre-gelatinized starch, and the like; lubricants, such as hydrogenated vegetable oil, stearic acid and the like; diluents, such as lactose, mannose, and sucrose; disintegrants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

For preparing the formulations as described above, inert, pharmaceutically acceptable carriers are used which are either solid or liquid form. Solid form preparations include powders, tablets, dispersible granules, capsules, and cachets. A solid carrier is suitably one or more substances which may also act as diluents, flavoring agents, solubilizers, lubricants, suspending agents, binders or tablet disintegrating agents. The solid carrier material also includes encapsulating material. In powders, the carrier is finely divided active compounds. In the tablet, the active compound is mixed with the carrier having the necessary binding properties in suitable proportions and compacted in the shape and size desired. Suitable solid carriers include, but are not limited, to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compounds with encapsulating material as the carrier providing a capsule in which the active component (with or without other carriers) is surrounded by carrier, which is thus in association with it. Tablets, powders, cachets, and capsules may be used in a solid dosage form suitable for oral administration.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations which are intended to be converted, shortly before use, to liquid form preparations for either oral or parental administration. Such liquid forms include solutions, suspensions, and emulsions. These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric contained.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like, as well as combinations thereof. The liquid utilized will be chosen with regard to the route of administration.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients.

Determination of the proper dosage for a particular situation is within the skill of the art. For convenience, the total daily dosage may be divided and administered in portions during the day if desired. Controlled and uncontrolled release formulations are also included.

The energy drink or tablet could be taken as often as needed to increase energy. Bio-E formulations according to embodiments of the invention provide ideal conditions for physiological energy production. The bio-E formulations provide ideal conditions for making ATP while relying upon the body's own capacity for producing ATP. Addition of sugars and high calorie components are not necessary to obtain the effect. Accordingly, bio-E formulations may be used in weight loss and calorie burning.

Bio-E formulations have the advantage that they provide for release of energy without additives such as caffeine. The components are all natural, physiological biomolecules and ions that rely upon stimulation of the user's own system to release energy and possibly promote weight loss.

EXAMPLE 1

Exemplary Trigger Complex

A non-limiting example of a Trigger Complex with the active ingredients is shown in the following Table 1.

TABLE 1

| Active Ingredient | Effective range (mg) | Preferred range (mg) | Per Serving (mg) |
| --- | --- | --- | --- |
| Lactoferrin | 0.001-10,000 | 5-500 | 30 |
| Sodium bicarbonate | 0.1-10,000 | 10-1000 | 200 |
| Potassium bicarbonate | 0.1-10,000 | 10-1000 | 200 |
| Magnesium (II) | 1-1000 | 4-400 | 40 |
| Citric acid | 0.1-10,000 | 10-1000 | 200 |
| Maltodextrin | 10-100,000 | 100-10,000 | 1500 |

The above ingredients are mixed/milled to a fine blend as is or in combination with the ingredients of the Elemental Complex and/or the Coenzyme/Vitamin-B complex to make the final blend. LF could be used in free-dispersed native form (fdn) or could be used as admixtures of metal-unsaturated, partially saturated and fully saturated LF forms. The above LF preparations further processed to LF-(TCR) form is the most preferred ingredient suitable for the bio-E applications. Depending upon the required viscosity of the aqueous phase, the amounts of maltodextrin and/or other insoluble acid-resistant fibers could be adjusted.

EXAMPLE 2

Exemplary Elemental Complex

The following essential elements with the indicated state of valency are used. The amounts presented in per serving column are the recommended daily allowance (RDA) for each active element. Based on the salt form used the actual weight of the ingredient may vary to maintain the per serving value. Accordingly, when iron is used as a citrate form (with 17% iron) or as a gluconate form (with 10% iron), the total weight of the salt is 70.4 mg and 120 mg, respectively. However, the active iron content for either of these two salts is 12 mg (100% DV).

A non-limiting example of an Elemental Complex with active ingredients is shown in the following Table 2.

TABLE 2

| Active Element | Effective range (mg) | Preferred range (mg) | Per Serving (mg) |
| --- | --- | --- | --- |
| Iron (III) | 0.01-500 | 0.1-50.0 | 12.0 |
| Copper (II) | 0.1-100 | 0.02-20.0 | 2.0 |

TABLE 2-continued

| Active Element | Effective range (mg) | Preferred range (mg) | Per Serving (mg) |
| --- | --- | --- | --- |
| Zinc (II) | 0.01-500 | 0.1-50.0 | 15.0 |
| Chromium (II) | 0.1-100 | 0.01-10.0 | 0.12 |
| Manganese (II) | 0.1-100 | 0.02-20.0 | 2.0 |

All ingredients from the above composition are mixed/milled to a fine blend as is or combined with the ingredients of the Trigger Complex and/or the Coenzyme/Vitamin-B complex to make the final blend.

The active elements, iron(III) and copper(II) in particular, could be further incorporated as metallo-LF complexes in the blend. The iron and copper metal complexes of LF are prepared from stock solutions of known concentration of apo-LF in 0.05M Tris-HCl, pH 7.4, followed by sequential addition with known aliquots of 0.1M bicarbonate and either Fe(III) or Cu(II) ions. The Fe(III) complexes was prepared by mixing equimolar amount of ferric nitrate with disodium salt of nitriloacetic acid. Cu(II) complexes were prepared by addition of aqueous copper chloride to apo-LF. Metal complexes were allowed to equilibrate for 2-24 h. Absorbance spectra were run on all metallo-LF complexes in the visible region to determine the extent of metal saturation of the protein. Concentrations of the Fe(III)-LF and Cu(II)-LF were determined using extinction coefficients of 14.3 and 12.5 at 280 nm, respectively (Ainscough E W, et al. Spectroscopic studies on Cu(II) complexes of human lactoferrin. J Inorg Biochem 18:103-112, 1983).

EXAMPLE 3

Exemplary Coenzyme/Vitamin B-Complex

A non-limiting example of a Coenzyme/Vitamin B-Complex with active ingredients is shown in the following Table 3.

TABLE 3

| Active Ingredient | Effective range (mg) | Preferred range (mg) | Per Serving (mg) |
| --- | --- | --- | --- |
| Coenzyme Q10 | 0.01-1000 | 0.1-100 | 10.0 |
| Coenzyme I (NADH) | 0.01-1000 | 0.1-100 | 1.0 |
| Coenzyme R | 0.001-10 | 0.01-1.0 | 0.15 |
| Vitamin B1 | 0.01-1000 | 0.1-100 | 1.5 |
| Vitamin B2 | 0.01-1000 | 0.1-100 | 1.7 |
| Vitamin B3 | 0.1-10,000 | 1-1000 | 20.0 |
| Vitamin B5 | 0.1-10,000 | 1-1000 | 10.0 |
| Vitamin B6 | 0.01-1000 | 0.1-100 | 2.0 |
| Vitamin B12 | 0.0001-1 | 0.001-0.1 | 0.006 |
| Vitamin B9 | 0.001-10 | 0.01-1.0 | 0.2 |

Bioactive compounds such as D-ribose, L-carnitine, L-arginine and quercetin serve as synergists and could enhance the coenzyme activity. D-ribose is a naturally occurring five-carbon sugar found in all living cells. Some of the most important biological molecules contain D-ribose, including ATP, all the nucleotides and nucleotide coenzymes and all forms of RNA (ribonucleic acid). Ribose phosphates are components of the nucleotide coenzymes and are utilized by organisms in the synthesis of the amino acid histidine. Its close relative, deoxyribose, is a constituent of deoxyribonucleic acid (DNA), where it alternates with phosphate groups to form the 'back-bone' of the DNA polymer and binds to nitrogenous bases. The presence of deoxyribose instead of ribose is one difference between DNA and RNA. Ribose has one more oxygen atom in its molecule than deoxyribose. Ribose has a five member ring composed of four carbon atoms and a singlet oxygen. Hydroxyl groups are attached to three of the carbons. The other carbon and a hydroxyl group are attached to one of the carbon atoms adjacent to the oxygen. In deoxyribose, the carbon furthest from the attached carbon is stripped of the oxygen atom in what would be a hydroxyl group in ribose. The sugar (ribose or deoxyribose) molecules in the nucleic acid are all oriented in the same direction. Their carbon atoms are numbered: the 5' carbon atom is always on the side of the sugar molecule that faces the leading end, while the 3' carbon atom always faces the tail end. Nucleotide is the structural unit of a nucleic acid. A nucleotide consists of either a nitrogenous heterocyclic base (purine or pyrimidine), a pentose sugar (ribose or deoxyribose) and a phosphate group attached at the 5' position on the sugar. A nucleoside consists of only a pentose sugar linked to a purine or pyrimidine base, without a phosphate group. The nucleoside derivatives are involved in important functions in cellular metabolism (eg. ATP-dependent bio-E process) and in the synthesis of enzyme regulators, antimicrobial and antitumor agents.

L-carnitine is found in all mammalian tissue, especially striated muscle, and is synthesized in the liver, kidneys, and brain from the amino acids lysine and methionine. Approximately 98% of L-carnitine in the body is found in cardiac and skeletal muscle, with the remaining 2% being stored in the brain, kidney, and liver. It plays an important role in the transport of free fatty acids across the mitochondrial membrane for energy production, in the beta oxidation of fatty acids, and in maintaining an adequate ratio of fatty acetyl-CoA compounds to free CoA inside mitochondria. L-carnitine also indirectly activates the enzyme pyruvate dehydrogenase which is the rate limiting enzyme.

Different forms and derivatives of L-carnitine suitable for the bio-E formulations of the present invention include but not limited to L-carnitine fumarate, L-carnitine tartarate, acetyl L-carnitine, propionyl L-carnitine and amino carnitines.

Arginine is a component of collagen that plays a vital role in the production of new tissue and bone cells. Arginine is also involved in the production of variety of enzymes and hormones. It facilitates the release of human growth hormone (HGH), stimulates the pancreas for insulin production, and is a component in the hormone vasopressin produced by the pituitary gland. HGH-release by arginine could facilitate recovery from fractures and injuries, as well strengthening the immune system, building lean muscle, burning fat, and reversing many of the effects of aging. This essential amino acid is required for muscle metabolism due to its role in the transport, storage, and elimination of nitrogen. Creatine is derived from arginine, as are guanidophosphate and phosphoarginine, all of which have roles in muscle metabolism. The L-form of arginine is more compatible with human physiology and the only form recommended. L-arginine is a substrate for nitric oxide synthase (NOS) enzyme, which in the vascular endothelial cells converts L-arginine to nitric oxide. Nitric oxide is also known as endothelium-derived relaxation factor (EDRF), which causes vasodilation (Tenebaum A, Fisman E Z, Motro M. L-arginine—rediscovery in progress. Cardiology 90:153-155, 1998).

Quercetin is a water-soluble flavonoid with antihistamine and anti-inflammatory properties. Due to its antioxidant effect, quercetin has been suggested to inhibit inflammatory processes mediated by leukotrienes, hyaluronidase (collagen-destroying enzymes), and lysosomal enzymes. Quercetin could enhance the collagen network (structural integrity) of blood vessels, and is known for its antimicrobial activity. Quercetin has been suggested to alter intestinal cell homeostasis of copper, iron and manganese. Also quercetin may inhibit collagen and ADP-induced platelet aggregation (Janssen K, et al., Effects of the flavonoids quercetin and apigenin on homeostasis in healthy volunteers—results from an in vitro and a dietary supplement study. Am J Clin Nutr 67:255-262, 1998).

The admixtures of three complexes (trigger, elemental and coenzyme/vitamin-B) form a potent bio-E generating system. These admixtures could be incorporated into various delivery systems, including but not limited to, tablets (chewables, effervescent), caplets, capsules, powders, energy drinks, energy bars, infusions, and other forms that are commonly practiced in the art of manufacturing nutritionals, supplements and therapeutics for total body health and clinical nutrition.

EXAMPLE 4

Exemplary Admixing of the Three Complexes (Components) of Bio-E System

Admixing of the three components of bio-E system, i.e., the elemental, the coenzyme/vitamin and the trigger complexes in compositions of different health supplements with typical serving sizes such as a tea spoon (~4.5 g), table spoon (~8.0 g) or scoop (~35.0 g) is shown in the following Table 4 as a non-limiting example.

TABLE 4

| Complex/Ingredient | Compositional Percentage (wt/wt) per Serving | | | |
|---|---|---|---|---|
| | Range | 4.5-g | 8.0-g | 35.0-g |
| Elemental Complex | 0.5-10.0% | 1.1% | 0.6% | 0.1% |
| Coenzyme/Vitamin Complex | 0.5-10.0% | 1.1% | 0.6% | 0.1% |
| Trigger Complex | 10.0-75.0% | 46.0% | 36.2% | 8.3% |
| "Other" Functional Ingredients | 1.0-75.0% | 4.5% | 31.2% | 72.3% |
| Excipients | 5.0-50.0% | 47.3% | 31.4% | 19.2% |

Excipients suitable for bio-E containing compositions include but not limited to colorants, flavorings, gelling agents, dispersing agents, preservatives, effervescent systems, and other compounds commonly used in the manufacturing of tablets, hard-shell capsules, soft-gel capsules, syrups, drinks, elixirs, powder blends, nutritional bars, etc.

"Other" functional ingredients include bioactive compounds intended to deliver specific health, nutraceutical and/or metabolic effects when administered to a host. Specific functional ingredients or ingredient systems can be admixed with bio-E containing compositions to promote specific health benefits.

EXAMPLE 5

Exemplary Energy Drink Formulation with Bio-E

Powder forms of the bio-E compositions can be administered by mixing the powdered composition in liquids such as water or milk and drinking the resultant mixture. A non-limiting example of a base (active) composition of the present invention for incorporation into an effervescent powder form is described in Table 5.

TABLE 5

| Complex/Ingredient | Composition per Serving Amount | % wt/wt |
|---|---|---|
| ELEMENTAL COMPLEX | (0.05 g)* | 1.1% |
| Iron (17% ferrous citrate) | 0.018 g | |
| Copper (50% as cupric citrare) | 0.001 g | |
| Zinc (15% as zinc gluconate) | 0.025 g | |
| Chromium (12% as chloride salt) | 250 mcg | |
| Manganese (12% as gluconate salt) | 0.004 g | |
| COENZYME COMPLEX | (0.05 g)* | 1.1% |
| Coenzyme Q10 | 0.01 g | |
| Coenzyme R (as Biotin) | 150 mcg | |
| Vitamin B1 (as Thiamine HCl) | 0.002 g | |
| Vitamin B2 (as Riboflavin) | 0.002 g | |
| Vitamin B3 (as Niacin/Niacinamide) | 0.02 g | |
| Vitamin B5 (as Calcium pantothenate) | 0.01 g | |
| Vitamin B6 (as Pyridoxine HCl) | 0.002 g | |
| Vitamin B9 (as Folic acid) | 200 mcg | |
| Vitamin B12 (as Cyanocobalamin) | 6 mcg | |
| TRIGGER COMPLEX | (2.07 g)* | 46.0% |
| Lactoferrin | 0.04 g | |
| Sodium bicarbonate | 0.1 g | |
| Potassium bicarbonate | 0.1 g | |
| Magnesium (31% as citrate) | 0.13 g | |
| Citric acid | 0.2 g | |
| Maltodextrin | 1.5 g | |
| FUNCTIONAL INGREDIENTS | (0.2 g)* | 4.5% |
| D-ribose | 50 mg | |
| L-arginine HCl | 100 mg | |
| Acetyl L-carnitine | 50 mg | |
| EXCIPIENTS | (2.13 g)* | 47.3% |
| Total weight* | 4.5 g* | 100% |

Pharmaceutically acceptable excipients including effervescent system, taste makers, natural flavor(s) and natural color(s) were blended with the ingredients exemplified above. Accordingly, each of the above ingredients was placed, in powdered form, into a commercial blender, mixed and, if necessary, passed through a mesh screen to remove aggregates.

Alternatively, the above formulation may be prepared as a soft gel or soft gelatin capsules by dispersion of the bio-E blend in an appropriate vehicle to form a high viscosity mixture, by using conventional methods well known in the art. Soft elastic gelatin capsules have a soft, globular gelatin shell, somewhat thicker than that of hard gelatin capsules. In such soft gel formats, gelatin is plasticized by the addition of plasticizing agent, e.g., glycerin, sorbitol, or a similar polyol. The hardness of the capsule shell can be altered with appropriate type of gelatin and the amounts of plasticizer and water. Soft gelatin shells may contain a preservative, such as methyl- and propylparabens and sorbic acid, to prevent any fungal growth. The bio-E formulation may be dissolved or suspended in a liquid vehicle or carrier, such as vegetable or mineral oils, glycols such as polyethylene glycol and propylene glycol, triglycerides, surfactants such as polysorbates, or a combination thereof. Typically, the weight of the capsule may range between about 100 to 2500 milligrams; in particular, weigh between about 500 and 2000 milligrams; and more specifically, weigh between about 750 and 1500 milligrams.

An orange-flavored powdered drink mix was prepared using the formulation of Table 5 for the bio-E energy drink. The bio-E drink was administered to about 20 individual testers as 8 oz. servings. In a typical response of the bio-E testers, there was a thermogenic response within 5 min after consumption of the drink followed by an increase in thirst about 30 minutes later. In a control group of 20 individuals who received a market available energy drink, these effects were not observed. Typically, the bio-E drink testers reported enhanced alertness in less than 5 min after taking the drink, which lasted for 4-5 hours.

EXAMPLE 6

Exemplary Bio-E Formulation for Weight Management

In the following example, a formulation designed to facilitate weight loss is presented. The weight management compositions of the present invention may be provided in a variety of formats, including but not limited to, liquid form, powder form, protein bar or trail mix form. Powders are preferable and are prepared to be suitable for mixing with water or other liquids. The weight loss compositions in powder or granular form may be provided in accordance with customary processing techniques, for example as spray dried powders, or the like.

TABLE 6

| Complex/Ingredient | Composition per Serving Amount (g) | % wt/wt |
|---|---|---|
| ELEMENTAL COMPLEX | (0.05 g)* | 0.6% |
| COENZYME COMPLEX | (0.05 g)* | 0.6% |
| TRIGGER COMPLEX (bio-E) | (2.9 g)* | 36.2% |
| Lactoferrin-(TCR) | 0.04 g | |
| Sodium bicarbonate | 0.2 g | |
| Potassium bicarbonate | 0.2 g | |
| Magnesium (31% as citrate) | 0.13 g | |
| Citric acid | 0.33 g | |
| Maltodextrin | 1.0 g | |
| Glucomannan | 1.0 g | |
| FUNCTIONAL INGREDIENTS | (2.5 g)* | 31.2% |
| Dihydroxy acetone | 0.05 g | |
| Inositol | 0.15 g | |
| 5-HTP (from *Griffonia simplicifolia*) | 0.15 g | |
| Choline (as bitartrate) | 0.05 g | |
| Milk protein concentrate | 0.1 g | |
| Pyruvate | 2.0 g | |
| EXCIPIENTS | (~2.5 g)* | 31.4% |
| Total weight* | ~8.0 g | 100% |

As shown above in Table 6, the Trigger Complex is reformulated with the addition of glucomannan to suit the weight management formula. Glucomannan is a polysaccharide derived from tubers of konjac plant (*Amorphophallus konjac*). Like many soluble fibers, glucomannan binds to a variety of substances in the gut to slow digestion, relieve constipation and reduce the absorption of fat and carbohydrates. It helps in weight loss, improves lipid profile as well as glucose tolerance in obese individuals. Glucomannan could also reduce total serum cholesterol in healthy individuals and in adults with overweight and diabetes. These activities are reportedly due to inhibition of active transport of cholesterol in the jejunum and absorption of bile acids in the ileum.

Other functional ingredients in the weight management formula may include but not limited to dihydroxy acetone, inositol, 5-HTP, choline, milk powder concentrate, and pyruvate. 5-HTP is a derivative of tryptophan, an amino acid in the body that converts to serotonin, a potent neurotransmitter in the brain. Furthermore, tryptophan, also breaks down in the body to yield ribose and/or NAD, both associated with the production of bio-energy. 5-HTP can increase serotonin levels in the body and influence mood, sleep patterns and pain control. 5-HTP used in the dietary supplementation is derived from the seeds of *Griffonia simplicifolia*, an African plant. Pyruvate reduces free radical production and decreases carbohydrate oxidation. Dietary supplementation with pyruvate and dihydroxy acetone increases arm and leg exercise endurance. The bio-E weight management formulation provides nutrition in the form of a milk protein and additional amino acids in combination with metal complexes and vitamins. By substitution of the above formulation for one or more meals, weight loss is achieved while maintaining or even increasing energy.

While the above formulation is described as a protein powder, in preferred embodiments, it may be formulated as a "weight loss bar" to approximate a meal-equivalent. Such weight loss bars may include rolled oats and bran mixed with the soy protein to form the common bar "oat-soy" material, to which the ingredients of bio-E formulation will be admixed with appetite-stimulants that may include high-fat and sour taste (eg: oil and vinegar); appetite-depressants that may include low-fat, fiber, and bitter taste (eg: starch, edible gum, and quinine). Alternative or additional ingredients may be carbohydrates derived from other grains, fruits, and vegetables; with proteins derived from nuts, beans, eggs, cheese, meat, fish, and fowl. Soluble and insoluble fiber sources include apples, potatoes, and gum plants. Vitamins, minerals, and other additives may be included.

The weight loss bar can be prepared, without limitation, by mixing bio-E blend with all the ingredients of the formulation with excipients (e.g., binders, fillers, flavors, colors, etc.) to a plastic mass consistency. The mass is then either extended or molded to form "rectangular bar" shapes that are then dried or allowed to solidify to form the final product. In preferred embodiments, these weight loss bars have a low to moderate Glycemic index (GI) to provide a sustained energy supply. Low-GI foods (less than 55) and moderate GI foods (55-70) produce a gradual rise in blood sugar that is compatible with the bio-E system. By providing formulations with a low or moderate GI index, sustained energy for daily activities is provided and a spike in blood sugar and insulin levels is avoided.

In some embodiments, the weight loss formulation may be provided as a Trail Mix. In some embodiments, the weight loss formulation is provided in combination with a DVD or instruction sheet containing recommended exercises to provide a cardiovascular workout and muscle strengthening program to be used in conjunction with the weight loss formulation.

EXAMPLE 7

Exemplary Bio-E Formulation for Exercise Recovery

In a preferred embodiment, a modification of the above formulation is used. The derived bio-E formulation promotes tissue recovery after exercise while providing energy and preventing oxidation damage. Vascularization improves as body mass increases. This formulation is particularly useful for body builders including weight lifters, professional athletes and dancers, and particularly for increasing muscle mass. This formulation may be prepared as a powder to be added to milk, water, yogurt or other food substance as a nutritional supplement.

TABLE 7

| Complex/Ingredient | Composition per Serving Amount (g) | % wt/wt |
|---|---|---|
| ELEMENTAL COMPLEX | (0.05 g)* | 0.1% |
| COENZYME COMPLEX | (0.05 g)* | 0.1% |
| TRIGGER COMPLEX (bio-E) | (2.9 g)* | 8.3% |
| Lactoferrin-(TCR) | 0.04 g | |
| Sodium bicarbonate | 0.2 g | |
| Potassium bicarbonate | 0.2 g | |
| Magnesium (31% as citrate) | 0.13 g | |
| Citric acid | 0.33 g | |
| Maltodextrin | 1.0 g | |
| Glucomannan | 1.0 g | |
| FUNCTIONAL INGREDIENTS | (25.3 g)* | 72.3% |
| L-taurine | 1.0 g | |
| N-acetyl creatine | 5.0 g | |
| Dehydroepiandrosterone (DHEA) | 0.05 g | |
| Amino Acid blend (glycine, leucine, arginine) | 4.0 g | |
| Choline | 0.2 g | |
| Inositol hexanicotinate | 0.05 g | |
| Protein powder (milk, egg, whey, or soy) | 15 g | |
| EXCIPIENTS | (~6.7 g)* | 19.2% |
| Total weight* | 35.0 g | 100% |

Nitric oxide (NO) is essential for muscle contraction and dilation of blood vessels. This cellular function is vital for widening of blood vessels to support an increased blood flow for greater oxygen and nutrient delivery. Body builders, in particular, need such increase in blood flow for maximum oxygen and nutrient delivery. Taurine plays an important role in NO production, and is therefore, a useful supplement to maintain or increase NO production.

DHEA is an androgen (male sex hormone) produced in the adrenal glands, and is one of the main precursors of testosterone. DHEA levels can decline up to 90% with age, therefore, is often used to boost sex hormone levels, and used by athletes to boost testosterone levels. Studies have shown that supplementing 50-100 mg of DHEA per day help increase muscle mass and improve overall health condition.

The formulation can optionally contain human growth hormones (hGF) or hGF precursors and stimulators; testosterone or testosterone precursors (eg. androstenediol) and stimulators (extracts from *Tribulus terrestris* or *Avena sativa*).

EXAMPLE 8

Exemplary Bio-E Formulation for Diabetes Control

In a preferred embodiment, a modification of the 'bio-E weight management formulation' described in Example 6, is used for individuals suffering from a diabetic condition, a pre-diabetic condition or for persons at risk for diabetes. The risk of diabetes is lowered by weight loss in overweight individuals. Even extremely overweight people can lower the risk of diabetes by moderate weight reductions. Consequently, the use of a preferred embodiment of the 'bio-E weight management formulation' can significantly reduce the risk of diabetes in 'at risk' individuals and relieve symptoms of diabetes in individuals suffering from the disease, even without exercise.

In preferred embodiments, substitution of one meal per day with a formulation according to the present invention can significantly reduce risk of diabetes by lowering the fat intake for at risk individuals or individuals suffering from symptoms of diabetes.

Preferably, a healthy total fat intake should range from 25-30% of daily calories (less than 10 percent saturated fat). Use of the formulation exemplified in Table 8 is helpful in achieving this ideal range.

TABLE 8

| Complex/Ingredient | Composition per Serving | |
|---|---|---|
| | Amount (g) | % wt/wt |
| ELEMENTAL COMPLEX | (0.05 g)* | 0.1% |
| COENZYME COMPLEX | (0.05 g)* | 0.1% |
| TRIGGER COMPLEX (bio-E) | (5.6 g)* | 11.2% |
| Lactoferrin-(TCR) | 0.1 g | |
| Sodium bicarbonate | 0.1 g | |
| Potassium bicarbonate | 0.1 g | |
| Magnesium | 0.1 g | |
| Citric acid | 0.2 g | |
| Prickly pear cactus | 1.5 g | |
| Locust bean gum | 1.5 g | |
| Guar gum | 2.0 g | |
| FUNCTIONAL INGREDIENTS | (5.2 g)* | 10.4% |
| Vanadium (Vanadyl sulfate) | 0.01 g | |
| Banaba Extract (1% corosolic acid) | 0.05 g | |
| Cinnamon | 0.05 g | |
| Fenugreek (*Trigonella foenum*) seed extract | 0.04 g | |
| Gymnema Sylvestre | 0.05 g | |
| Blond psyllium | 5.0 g | |
| EXCIPIENTS | (39.1 g)* | 78.2% |
| Total weight* | 50 g | 100% |

As shown above in Table 8, the Trigger Complex of the bio-E system is reformulated with prickly pear cactus, locus bean gum and guar gum to suit the diabetes-support formulation.

Diabetes is associated with abnormally high levels of glucose-modified proteins bearing advanced glycation endproducts (AGEs) in tissue and plasma. Elevated AGEs could block the activity of endogenous antimicrobial agents and predispose the diabetic individuals to microbial infections. AGEs interact with two specific binding domains on LF molecule to inactivate the bacterial agglutination and antimicrobial activity of this protein. A common 17-18 amino acid cysteine loop was identified in LF molecule as AGE-Binding Cysteine-bounded Domain, (ABCD motif). Similar ABCD motifs are also present in other antimicrobial proteins such as defensins. Synthetic peptides corresponding to ABCD motifs in LF could bind competitively to AGEs and may provide a basis for the development of new approaches to prevent diabetic infections [Li, 1998]. Due to its critical role in diabetes, LF concentration in the trigger complex is increased to 100 mg per serving. (Li Y M. Glycation ligand binding motif in lactoferrin. Implications in diabetic infection. Adv Exp Med Biol 443:57-63, 1998).

Preferred embodiments of the formulation for control and prevention of diabetes has the following additional beneficial components. Chromium in the elemental complex plays a role in regulating the uptake of sugars into the cell. Chromium supplements (30-600 mcg a day) may be helpful to people suffering from diabetes or persons with a pre-diabetic condition. Chromium is preferably supplied as chromium picolinate or chromium histidine.

Low magnesium correlates with diabetes and risk of developing diabetes. Many people, especially older people, do not get enough magnesium. Preferred embodiments of the formulations contain 100-500 mg magnesium. In preferred embodiments, magnesium may be supplied as magnesium acetate, aspartate, carbonate, chloride, citrate, glycinate, hydroxide, lactate, oxide, or pidolate.

Preferred embodiments of the invention include other functional ingredients such as the phytochemical extracts from banaba leaf, cinnamon bark, fenugreek seed and gymnema leaves. Banaba leaf extract contains a triterpenoid compound known as corosolic acid that stimulates glucose transport into cells. Banaba plays a role in regulating sugar and insulin levels in the blood. For certain individuals, fluctuations in blood sugar and insulin are related to appetite, hunger and various food cravings, particularly craving for carbohydrates such as bread and sweets. By maintaining the blood sugar and insulin levels in check, banaba may be an effective supplement for promoting weight loss. Cinnamon bark contains 60-80% of volatile oils, cinnamaldehyde in particular, which has been suggested for antispasmodic, antiflatulent, and appetite stimulant effects. Methyl-hydroxy chalcone polymer (MHCP), an active constituent of cinnamon has been reported to improve insulin sensitivity. Fenugreek seeds contain a high proportion (40%) of mucilage, a soluble fiber. Mucilage forms a gelatinous structure (similar to guar gum) that may have effects on slowing the digestion and absorption of food in the intestinal tract. Such effect could result in a slow and steady rise of blood sugar in certain diabetic individuals. Other compounds such as the saponins in fenugreek seeds may have a beneficial role in lowering the cholesterol production in the liver. *Gymnema sylvestre* leaves contain gymnemic acids, which are known to suppress glucose transport from the intestine to the blood stream. *Gymnema* also contains a small protein, gurmar, that can interact with receptors on the tongue to decrease the sensation of sweetness in many foods. This dual action has been shown to reduce blood sugar and cholesterol levels in diabetic individuals and may provide health benefits by controlling appetite and food cravings.

Preferred embodiments of the invention include one or more fibrous hydrocolloids. The fibrous polysaccharides of guar gum, locust bean gum and prickly pear cactus in the trigger complex and blond psyllium cumulatively decrease serum cholesterol levels by adsorbing dietary fats in the gastrointestinal tract and by reducing systemic absorption of the fat. The hydrocolloidal blend could induce hypoglycemic effects within 3-4 hours after ingestion of the formula and can last up to 6 hours. The fiber also seems to increase cholesterol elimination in fecal bile acids.

EXAMPLE 9

Exemplary Bio-E Formulation for the Control of Hyperlipidemia

The two primary lipids found in blood are cholesterol and triglycerides. An elevated level of these two lipid forms is generally referred to as hyperlipidemia, which is associated with increased risk of heart disease and stroke. Formulations according to embodiments of the present invention facilitate an optimal intake, metabolism of total fats and increased energy for physical activity. Both increased physical activity and regulation of fats obtained from dietary sources are useful strategies in coping with hyperlipidemia. A non-limiting example of a bio-E formula for control of hyperlipidemia is shown in Table 9.

TABLE 9

| Complex/Ingredient | Composition per Serving | |
|---|---|---|
| | Amount (g) | % wt/wt |
| ELEMENTAL COMPLEX | (0.05 g)* | 0.1% |
| COENZYME COMPLEX | (0.05 g)* | 0.1% |
| TRIGGER COMPLEX (bio-E) | (5.6 g)* | 11.2% |
| Lactoferrin-(TCR) | 0.1 g | |
| Sodium bicarbonate | 0.1 g | |
| Potassium bicarbonate | 0.1 g | |
| Magnesium | 0.1 g | |

TABLE 9-continued

| Complex/Ingredient | Composition per Serving | |
|---|---|---|
| | Amount (g) | % wt/wt |
| Citric acid | 0.2 g | |
| Prickly pear cactus | 1.5 g | |
| Locust bean gum | 1.5 g | |
| Guar gum | 2.0 g | |
| FUNCTIONAL INGREDIENTS | (5.6 g)* | 11.2% |
| Policosanol | 0.01 g | |
| Sitostanol | 0.08 g | |
| Octacosanol | 0.01 g | |
| Flaxseed Oil | 0.5 g | |
| Blond psyllium | 5.0 g | |
| EXCIPIENTS | (38.7 g)* | 77.4% |
| Total weight* | 50 g | 100% |

As shown above in Table 9, the Trigger Complex of the bio-E system is similar to the one described for diabetes control formulation described in Example 8. Furthermore, blond psyllium in the composition provides a similar hydrocolloidal format (with polysaccharides of the trigger complex) for the management of hyperlipidemia.

Other functional ingredients such as the phytosterols, including but not limited to, policosanol, sitostanol and octacosanol are incorporated in the bio-E hyperlipidemia-control formulation. Policosanol has been suggested to inhibit cholesterol synthesis in the liver. The Cuban sugar-cane-derived policosanol is reported to lower cholesterol, reduce the risk of blood clots and enhance circulation. Sitostanol, alone and in combination with other plant sterols, reduces blood cholesterol levels by blocking systemic absorption of triglycerides. Octacosanol, a 28-carbon waxy alcohol, improves oxygen utilization during anaerobic glycolysis and helps to remove lactic acid by increasing the efficacy of tricarboxylic acid cycle. Octacosanol also suppresses lipid accumulation in the adipose tissue and increases the mobilization of free fatty acids from fat cells in the muscle. Octacosanol could lower the LDL cholesterol levels and raise the HDL cholesterol levels by regulating the cholesterol production by liver. Preferred formulations for hyperlipidemia control may include alpha-linoleic acids and/or omega-3 fatty acids to lower both triglycerides and cholesterol.

EXAMPLE 10

Exemplary Bio-E Formulation for Celiacs

Celiac disease refers to a genetic inability to absorb gluten, a protein found in wheat, barley, rye, and some oat products. Exposure to gluten causes inflammation of the membrane that lines the small intestine. Besides abdominal pain and swelling, lack of energy results from the lessened ability to absorb nutrients.

In order to provide an energy supplementation for individuals with celiac conditions, bio-E can be formulated with gluten-free ingredients. The trigger complex and functional components of bio-E formulation could be selected from the list of ingredients that are compatible with the dietary requirements of individuals affected with celiac conditions.

EXAMPLE 11

Exemplary Bio-E Formulation for Immuno-Compromised Conditions

Bio-E formulations according to embodiments of the invention are beneficial for patients suffering from immuno-compromised conditions such as neutropenia, diseases of neutrophil dysfunction, chronic fatigue syndrome, radiation-associated side effects, and immune deficiency syndromes (e.g. AIDS). These immuno-compromised conditions manifest in lower energy levels due to disease symptoms or disease treatments.

Besides manifesting a low physiological energy state, neutrophil deficiency and/or dysfunction is one of the major underlying conditions in the immuno-compromised host. Body levels of several neutrophil secretory components (eg. LF, superoxide dismutase, lysozyme, peroxidases) that are essential for protection against harmful pathogens and allergens may be diminished or absent during immuno-compromised conditions. Therefore, the bio-E formulation of the present invention has been enriched with natural host defense factors to provide protection to the immuno-compromised host from potential infections. A non-limiting example of bio-E formulation for the support of immuno-compromised host is shown in Table 10.

TABLE 10

| Complex/Ingredient | Composition per Serving | |
|---|---|---|
| | Amount (g) | % wt/wt |
| ELEMENTAL COMPLEX | (0.05 g)* | 1.1% |
| COENZYME COMPLEX | (0.05 g)* | 1.1% |
| TRIGGER COMPLEX (bio-E) | (2.13 g)* | 47.3% |
| Lactoferrin-(TCR) | 0.1 g | |
| Sodium bicarbonate | 0.1 g | |
| Potassium bicarbonate | 0.1 g | |
| Magnesium (31% as citrate) | 0.13 g | |
| Citric acid | 0.2 g | |
| Lecithin | 0.1 g | |
| Maltodextrin | 1.5 g | |
| FUNCTIONAL INGREDIENTS | (1.0 g)* | 22.2% |
| Superoxide dismutase (SOD) | 0.025 g | |
| Lysozyme (from hen egg) | 0.025 g | |
| Lactoperoxidase (from cow milk) | 0.025 g | |
| L-theanine (from Green tea) | 0.025 g | |
| Vitamin-E (α-D-tocopheryl acetate) | 0.1 g | |
| Blond psyllium | 0.6 g | |
| EXCIPIENTS | (~1.3 g)* | 28.3% |
| Total weight* | (4.5 g)* | 100% |

As shown above in Table 10, the bio-E formula is enriched with functional ingredients such as antimicrobial agents (eg. LF, lactoperoxidase (LPO), and lysozyme (LZ)) and antioxidants (eg. superoxide dismutase (SOD), L-theanine and vitamin-E).

Superoxide dismutase (SOD) is an essential enzyme found in all living cells. It catalyzes the conversion of toxic superoxide to oxygen and hydrogen peroxide. The action of SOD is believed to prevent oxygen-related damage to body tissues. The SOD useful in accordance with the present invention include SOD extracted from melon fruit, commercially available from Isocell Nutra, France.

Lysozyme (LZ) also known as muraminidase is ubiquitous in both the animal and plant kingdoms, which plays an important role in the natural defense mechanism. LZ is a potent antimicrobial system that promotes catalysis by inducing steric stress in the substrate, most effective against gram-positive bacteria. The LZ useful in accordance with the present invention include LZ isolated from hen egg, commercially available from Inovatech, Canada.

Lactoperoxidase (LPO) is a hemoprotein also present in milk, tears, and saliva. LPO constitutes one of the non-immunoglobulin defense factors in the mucosal secretions. LPO catalyzes the oxidation of electron donors by peroxide to generate highly reactive products with a wide range of antimicrobial properties. The LPO useful in accordance with the present invention include LPO isolated from mammalian sources (humans, cows, sows, mares, transgenic animals and the like), biological secretions such as colostrum, transitional milk, matured milk, milk in later lactation, and the like, or processed products thereof such as skim milk and whey. Suitable LPO is available from various commercial sources (Tatua or Fonterra from New Zealand, Morinaga Milk Company from Japan, DMV International from the Netherlands).

EXAMPLE 12

Exemplary Bio-E Formulation for Detoxification Support

Bio-E formulations according to the invention are beneficial for any person going through detoxification or drug withdrawal, including but not limited to withdrawal from nicotine, alcohol, pain killers, and opiates because they provide optimal conditions for the body to use its own resources to provide energy in the form of ATP and because formulations according to the invention include additional components to promote overall good health.

Most detoxification conditions, colon cleansing systems in particular, could eliminate several host mucosal components, nutrients and beneficial probiotic bacteria from the physiological system. Therefore, it is important to refurbish the microenvironment of the mucosal system that has undergone the detoxification process. Furthermore, during the recovery phase following the detoxification procedure, it is necessary to protect the treated physiological system with appropriate defense factors. Accordingly, the bio-E system of the present invention has been formulated with probiotic lactic acid bacteria (eg. *Lactobacillus* spp. and *Bifidobacterium* spp.) to reinforce the physiological system that has undergone a detoxification process. A non-limiting example of bio-E formulation for the supplementation of detoxification systems is shown in Table 11.

TABLE 11

| Complex/Ingredient | Composition per Serving | |
|---|---|---|
| | Amount (g) | % wt/wt |
| ELEMENTAL COMPLEX | (0.05 g)* | 0.6% |
| COENZYME COMPLEX | (0.05 g)* | 0.6% |
| TRIGGER COMPLEX (bio-E) | (1.7 g)* | 21.2% |
| Lactoferrin-(TCR) | 0.1 g | |
| Sodium bicarbonate | 0.2 g | |
| Potassium bicarbonate | 0.1 g | |
| Magnesium (31% as citrate) | 0.1 g | |
| Citric acid | 0.2 g | |
| Maltodextrin | 1.0 g | |
| FUNCTIONAL INGREDIENTS | (4.15 g)* | 51.9% |
| *Lactobacillus* spp. (50 billion CFU/g) | 0.25 g | |
| *Bifidobacterium* spp. (50 billion CFU/g) | 0.25 g | |
| L-theanine (green tea extract) | 0.05 | |
| Cranberry extract | 0.05 | |
| Turmeric root extract | 0.05 | |
| Inulin | 0.5 g | |
| Blond psyllium | 3.0 g | |
| EXCIPIENTS | (~2.06 g)* | 25.7% |
| Total weight* | 8 g | 100% |

As shown above in Table 11, the bio-E formula is supported with prebiotic systems (eg. LF and inulin), probiotic flora (eg. *Lactobacillus* spp., *Bifidobacterium* spp.) and antimicrobial/antioxidant systems (eg. cranberry and turmeric root extracts).

The formulations of the present invention can further include probiotic lactic acid bacteria (LAB) in a viable cell preparation or a non-viable cell preparation in the form of a freeze-dried powder or an emulsion for delivery with bio-E formulations.

The probiotic organisms envisaged in accordance with this invention include a physiologically effective dosage of at least one LAB strain, typically in the form of a freeze-dried powder or emulsion, such as the strains of bacteria of the genus *Lactobacillus* including *L. acidophilus, L. amylovorus, L. animalis, L. bavaricus, L. brevis, L. bulgaricus, L. casei* spp *casei, L. casei* spp *rhamnosus, L. crispatus, L. delbrueckii* ssp *lactis*, L. eichmanni, *L. fermentum, L. helveticus, L. jensenii, L. kefir, L. paracasei, L. pentosus L. plantarum, L. reuteri, L. salivarius*, and *L. sake*; the genus *Leuconostoc* including *Leu. cremoris* and *Leu. lactis*; the genus *Bifidobacterium* including *B. adolescentis, B. animalis, B. bifidum, B. breve, B. infantis, B longum*, and *B. thermophilum*; the genus *Pediococcus* including *Ped. acidilactici* and *Ped. pentosus*; the genus *Peptostreptococcus* including *Pep. asaccharolyticus*, and *Pep. productus*; the genus *Propionibacterium* including *Pro. acidipropionici, Pro. freudenreichii, Pro. jensenii*, and *Pro. theonii*; the genus *Streptococcus* including *S. cremoris, S. faecium, S. lactis, S. raffinolactis*, and *S. thermophilus*. The probiotic organisms are collectively known as "lactic acid bacteria"; or "LAB".

The effective dosages of probiotic in a mixed composition range between $10^2$ to $10^{12}$ colony forming units; preferably between $10^5$ to $10^{10}$ colony forming units per serving. Wherein the non-viable counts of probiotic in a mixed composition range between $10^2$ to $10^{12}$ colony forming units; preferably between $10^5$ to $10^{10}$ colony forming units per serving.

Although the above supplements have been described with reference to specific formulations, it will be recognized that these supplements may be included in other formulations as disclosed herein for their well known benefits.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A composition to facilitate weight loss in an individual comprising:
   a trigger complex comprising Lactoferrin (LF) comprising a zinc ion covalently bound to the LF, magnesium, citric acid, glucomannan and at least one additional hydrocolloid compound at alkaline pH,
   an elemental complex comprising a zinc metal salt, and
   a coenzyme complex comprising at least one coenzyme or coenzyme precursor, wherein the concentration of LF in the composition is from 0.2 to 5% (wt/wt).

2. The composition of claim 1, wherein the lactoferrin is lactoferrin treated for contamination reduction (LF-TCR).

3. The composition of claim 1, wherein the additional hydrocolloid compound is selected from the group consisting of edible celluloses, arabinogalactans, β-glucans, arabinoxylans, glucuronoxylans, xyloglucans, galactomannans, methyl cellulose, hydroxypropylmethyl cellulose (HPMC), inulin, oligofructans, xanthan gum, guar gum, locust bean gum, gum acacia, gum karaya, gum tragacanth, resistant starches, maltodextrins, chemically synthesized polydextrose, lactulose, cellulose derivatives, methyl cellulose, hydroxypropylmethylcellulose, egg lecithin, soybean lecithin, vegilecithin, vitellin, short chain fructooligosaccharides (FOS), transgalactooligosaccharides (TOS), levan, oligofructose, xylooligosaccharides (XOS), curdlan, chitin, chitosan, collagen and chondroitin.

4. The composition of claim 1, wherein the alkaline pH is provided by a carbonate/bicarbonate buffer system.

5. The composition of claim 1, wherein the additional hydrocolloid is selected from the group consisting of maltodextrins, chitin, chitosan, cellulose derivatives, guar gum, locust bean gum, prickly pear cactus and combinations thereof.

6. The composition of claim 1, wherein the coenzyme complex comprises one or more cofactor selected from the group consisting of coenzyme Q10, NADH, NADPH, coenzyme R and B-complex vitamins.

7. The composition of claim 6, wherein the B-complex vitamins are selected from the group consisting of Vitamin B1, Vitamin B2, Vitamin B3, Vitamin B5, Vitamin B6, Vitamin B9, Vitamin B12, and combinations thereof.

8. The composition of claim 1, further comprising D-ribose, L-arginine, L-carnitine or combinations thereof.

9. A food or beverage comprising the composition of claim 1.

10. A formulation to facilitate weight loss in an individual comprising:
an elemental complex comprising zinc;
a coenzyme complex comprising at least two selected from the group consisting of coenzyme Q10, coenzyme R, Vitamin B1, Vitamin B2, Vitamin B3, Vitamin B5, Vitamin B6, Vitamin B9, and Vitamin B12;
a trigger complex comprising a dietary fiber which comprises glucomannan, zinc-lactoferrin and a bicarbonate buffer, wherein zinc-LF comprises zinc ion covalently linked to the LF, and wherein the concentration of LF in the composition is from 0.2 to 5% (wt/wt); and
at least two of the following ingredients: dihydroxy acetone (DHA), inositol, 5-hydroxy-L-tryptophan (5-HTP), choline, milk protein hydrolysate, and pyruvate.

11. The composition of claim 10, wherein the lactoferrin is LF-TCR.

12. The formulation to facilitate weight loss according to claim 10, further comprising magnesium.

13. The formulation of claim 1, wherein the lactoferrin concentration is 50-500 mg per serving.

14. A method to facilitate weight loss which comprises administering a bar comprising the formulation of claim 10 as a meal supplement.

15. A method to facilitate weight loss which comprises mixing the formulation of claim 10 with milk or water and drinking the mixture as a meal supplement.

16. A method of facilitating weight loss comprising substituting a food or drink comprising the formulation of claim 10 for one or more meals per day.

* * * * *